(12) United States Patent
Dong et al.

(10) Patent No.: US 12,290,296 B2
(45) Date of Patent: May 6, 2025

(54) BONE FIXATION SYSTEM CAPABLE OF GRADUALLY CHANGING FROM RIGID FIXATION TO AXIAL NON-RIGID FIXATION

(71) Applicant: Xieping Dong, Nanchang (CN)

(72) Inventors: Xieping Dong, Nanchang (CN); Qingli Li, Nanchang (CN); Jingna Li, Yongzhou (CN); Zizheng Ai, NanChang (CN); Yuxiang Mei, JiuJiang (CN); Qunming Bian, NanChang (CN); Weiyi He, GuangZhou (CN)

(73) Assignee: Xieping Dong, Nanchang (CN)

( * ) Notice: Subject to any disclaimer, the term of this patent is extended or adjusted under 35 U.S.C. 154(b) by 569 days.

(21) Appl. No.: 17/630,772

(22) PCT Filed: Jul. 2, 2020

(86) PCT No.: PCT/CN2020/100008
§ 371 (c)(1),
(2) Date: Jan. 27, 2022

(87) PCT Pub. No.: WO2022/000440
PCT Pub. Date: Jan. 6, 2022

(65) Prior Publication Data
US 2022/0265331 A1 Aug. 25, 2022

(51) Int. Cl.
*A61B 17/80* (2006.01)
*A61B 17/86* (2006.01)
(52) U.S. Cl.
CPC .............. *A61B 17/86* (2013.01); *A61B 17/80* (2013.01)

(58) Field of Classification Search
CPC ........................... A61B 17/80; A61B 17/8004
See application file for complete search history.

(56) References Cited

U.S. PATENT DOCUMENTS

| | | | |
|---|---|---|---|
| 2005/0085812 A1 | 4/2005 | Sherman et al. | |
| 2007/0161997 A1 | 7/2007 | Thramann et al. | |
| 2010/0063505 A1* | 3/2010 | Frigg | A61B 17/8004 606/71 |
| 2018/0070997 A1 | 3/2018 | Bottlang et al. | |
| 2020/0000501 A1* | 1/2020 | Gephart | A61B 17/8047 |

FOREIGN PATENT DOCUMENTS

| | | |
|---|---|---|
| CN | 101862217 A | 10/2010 |
| CN | 107260292 A | 10/2017 |
| CN | 108210049 A | 6/2018 |

OTHER PUBLICATIONS

International Search Report from International Application No. PCT/CN2020/100008 mailed Mar. 25, 2021.

* cited by examiner

*Primary Examiner* — Olivia C Chang
(74) *Attorney, Agent, or Firm* — Zhigang Ma

(57) ABSTRACT

The present disclosure discloses a limb bone fixation system capable of automatically transforming from AO (Association for Study of Internal Fixation) to BO (Bio-logical Osteosynthesis) elastic fixation. The system includes a bone nail, a bone bridge, and connecting pieces attached to the bone bridge. The bone bridge is divided into a plate-shaped bone bridge and a rod-shaped bone bridge. A gasket made of a rigid degradable biomaterial is added between all connecting pieces at a broken end of one side of a fracture and the bone bridge, which can form rigid fixation for the fracture at initial fixation.

7 Claims, 16 Drawing Sheets

BONE FIXATION SYSTEM CAPABLE OF GRADUALLY CHANGING FROM RIGID FIXATION TO AXIAL NON-RIGID FIXATION

TECHNICAL FIELD

The present disclosure relates to the field of medical apparatuses and instruments, and in particular, to a bone fixation system capable of gradually changing from rigid fixation to axial non-rigid fixation.

BACKGROUND ART

After more than 50 years of evolution, an international mainstream fracture fixation manner has changed from an AO (Association for Study of Internal Fixation) theory and apparatuses and instruments of rigid fixation into a BO (Bio-logical Osteosynthesis) theory and apparatuses and instruments of elastic fixation. However, from the perspective of a fracture healing process, rigid fixation in an early period can prevent the displacement of fractured ends and fixation failure, and provide conditions for early functional exercises. In middle and late periods of fracture healing, changing to elastic fixation with relatively weak fixation strength helps to reduce stress shielding of the fracture end and enable the fractured ends to obtain axial physiological stress stimulation conducive to bone healing, so as to improve the quality of bone healing and reduce disused osteoporosis under the scope of protection of a fixture. That is, in the early period of the fracture healing, rigid fixation is superior to elastic fixation, in the middle and late periods of the fracture healing, elastic fixation is superior to rigid fixation. However, it is limited that an implant which can provide sufficient fixation strength for a weight-bearing bone in an early period of fixation cannot be automatically transformed into elastic fixation in the middle and late periods, so the fixation strength needs to be reduced by a surgery. For example, after a fracture is fixed with an intramedullary nail, it is sometimes necessary to perform another minor surgery three months after the surgery to remove a locking nail at one end of the intramedullary nail, so as to transform initial static fixation into dynamic fixation. However, this manner is often unacceptable to patients. Patients with plate fixation have no practice of a second surgery unless nonunion or delayed union has occurred. Therefore, it is difficult to reduce the incidence rate of the delayed union, the nonunion, and re-fracture at present.

SUMMARY

An objective of the present disclosure is to overcome the shortcomings of the prior art, meet the needs of patients, and provide a bone fixation system capable of gradually changing from rigid fixation to axial non-rigid fixation that can gradually transform from rigid fixation to elastic fixation in vivo over time without a surgery, so as to realize automatic transformation from AO rigid fixation to BO elastic fixation.

The bone fixation system capable of gradually changing from rigid fixation to axial non-rigid fixation includes a bone bridge that is attached with connecting pieces and realizes fixation through a bone nail. The bone bridge spans fracture ends and is placed on bone surfaces on both sides of the fracture ends. The bone nail at the fracture end on one side fixes a bone to the bone bridge directly or through the connecting piece. The bone at the fracture end on the other side is fixed to the bone bridge by using the bone nail through the connecting pieces.

A degradable gasket made of a rigid degradable biological material is added between a joint of the connecting piece on the fracture end on the other side and the bone bridge. The bone nail, the connecting piece, the degradable gasket, the bone bridge, and two ends of a fractured bone fixedly connected by the bone bridge form a stable fracture/fixture complex at initial fixation, so as to form stable static fixation.

As the degradable gasket is gradually degraded and absorbed in vivo, the connection between the connecting piece where the degradable gasket is placed and the bone bridge gradually loosens therewith. However, the positional relationships between the bone nail and the bones on two sides of the fracture end and between the bone bridge and the bones on two sides of the fracture end are still stable rigid invariable structures, the combination between the connecting piece where only the gasket is placed and the bone bridge becomes clearance fit, and the fracture ends constrained by the bone bridge, the connecting piece, and the bone nail can also only slide axially along the bone bridge under the action of an external force. That is, the fracture/fixture complex becomes axial non-rigid connection; and the fixation of the whole fixation system also gradually changes to axial non-rigid dynamic fixation.

The bone bridge is a plate-shaped bone plate, and the bone plate includes a bone nail through hole and a chute.

The connecting piece is a sliding block embedded into the chute of the bone plate, and at least one bone nail through hole is formed in the sliding block.

A side wall of the sliding block is a smooth plane. The side wall of the sliding block is matched with an inner wall of the chute in a surface contact manner in a radial direction. There is a sliding clearance between the sliding block and the chute in the axial direction of the bone plate. The degradable gasket is located in the sliding clearance. The bone nail is connected with the bone plate through the bone nail through hole in the bone plate and the bone nail through hole in an upper surface of the sliding block attached to the bone plate with a smooth common nail head and a threaded locking nail head, so as to complete the assembly and fixation of the fracture/fixture system.

The chute is a through slot penetrating through a plate surface of the bone plate. A key slot is formed in one or two side walls of the sliding block. A key pin hole is formed in the side wall of the chute corresponding to the key slot. The axial length of the key slot along the sliding block is greater than the diameter of a key pin and allows relative movement of the key pin and the key slot. The key pin is fixedly connected to the interior of the key pin hole and extends into the key slot, so as to limit the sliding block to only perform axial translation movement in the through slot.

The chute is a through slot penetrating through the plate surface of the bone plate, a dovetail-shaped or rectangular bulge is formed in each of a left inner wall and a right inner wall of the sliding block, and groove belts matched with the budges are respectively formed in the inner walls of the through slot, so as to form matched tenon riveting structures of the dovetail-shaped or rectangular slots for connecting. The bulges are embedded into the groove belts and can slide in the groove belts, so as to limit the sliding block to only perform axial translation movement in the through slot.

The chute is a through slot penetrating through the plate surface of the bone plate. Two side walls of the sliding block and two inner walls of the through slot are all arc-shaped and are symmetrical concentric circles. The sliding block is embedded into the through slot in a rotating manner through a common axis of the sliding block and the through slot. The nail entering direction of the bone nail can be changed by deflecting the sliding block through the common axis when a fracture fixation surgical operation is performed. After a fixation surgery is completed, the two arc-shaped inner walls of the through slot enclose the two side walls of the sliding block, so as to limit the sliding block to only perform axial translation movement in the through slot.

A deformation seam formed in the axial direction of the sliding block is formed in the sliding block. The deformation seam enables a closed bone nail through hole in the sliding block to become a completely open or partially open bone nail through hole, so that the sliding block has a transverse elastic deformation condition. When the bone nail is screwed into the bone nail through hole, an extrusion pressure may be applied to side walls of the bone nail through hole on both sides of the deformation seam, and the two side walls of the sliding block can be prompted to extrude the inner wall of the through slot.

The completely open deformation seam completely penetrates through a side wall of the sliding block of the bone nail through hole; and the partially open deformation point is formed from shallow to deep or from an inner edge to an outer edge, but does not penetrate through the side wall of the sliding block.

The chute is a groove that does not penetrate through the plate surface of the bone plate, and the sliding block is embedded into the groove.

A through hole is formed in the bottom of the groove; the through hole is greater than the diameter of the bone nail; and when the degradable gasket is gradually degraded, the integrated sliding block and the fracture end of the bone may perform axial movement along the through hole along with the bone nail.

A laying-type degradable gasket which has the same shape as the bottom surface of the sliding block and is degradable is also arranged between the bottom of the sliding block and the groove. After the bone nail penetrates through the bone nail through hole in the sliding block and the laying-type degradable gasket is fastened in the bone, the connection between the sliding block and the bone plate is rigid connection.

The bone bridge is a rod-shaped connecting rod. The connecting piece is a connecting block. The connecting block is provided with a through hole for an implanting section of the bone nail to penetrate through and a rod clamping arm for fixing the connecting rod. After the connecting rod is constrained by the rod clamping arm of the connecting block, the connecting rod may be fixed to an outer surface of the bone by the bone nail penetrating through the through hole of the connecting block and the bone nail implanted into the bone. The degradable gasket is padded between the rod clamping arm and the connecting rod, so as to prevent the rod clamping arm from compressing the connecting rod directly. The bone nail, the connecting block, and the connecting rod or the degradable gasket together with the two fractured ends of the bone fixed by them form a stable rigid fracture/fixation complex.

The through hole in the connecting block is a smooth hole or a threaded hole, the rod clamping arm of the connecting block is adjacent to the through hole.

The bone nail consists of a front implanting section and a rear locking section. The implanting section of the bone nail is implanted into the bone. The locking section of the bone nail is connected to the through hole of the connecting block.

The degradable gasket is similar to a tile shape and is padded between the rod clamping arm and the connecting rod. The cross section of the degradable gasket is in a shallow arc shape smaller than a semicircle.

The through hole of the connecting block is the smooth hole. The locking section of the bone nail is a common nail head which is provided with a screwdriver interface at a rear end and is larger than the diameter of the smallest position of the smooth hole of the connecting block. The common nail head may be an integrated common nail head which is manufactured with the bone nail integrally, and may also be a combined common nail head that a compression nut is screwed with a nail body.

The smooth hole is divided into an upper part and a lower part. The upper part is a spherical surface with a large upper part and a small lower part. A lower end face of the common nail head of the locking section of the bone nail is a spherical surface matched with the spherical surface at the upper part of the smooth hole. The diameter of the implanting section of the bone nail is smaller than the minimum diameter of the smooth hole. The bone nail may swing conically within a scope constrained by a conical surface of the lower part of the smooth hole.

The through hole of the connecting block is a screw hole. Screw threads matched with the screw hole are formed in the locking section of the bone nail. The leads of the screw threads of the implanting section and the locking section of the bone nail are consistent.

There is one rod clamping arm or two rod clamping arms respectively located on two sides of the through hole. The manner of constraining the connecting rod by the rod clamping arm is semi-enclosed constraint that an end face of the rod clamping arm is free, or the rod clamping arm forms hoop-type fully-enclosed constraint on the connecting rod.

The block body of the connecting block is a whole body or is combined by overlaying a hook seat and a nail seat. When the connecting block is combined by the hook seat and the nail seat, the hook seat forms a lower half part of the connecting block, and has the rod clamping arm and the through hole. The through hole is a circular or ellipse-like shape through which the nail body of the bone nail can penetrate. The nail seat forms an upper half part of the connecting block, and has a through hole and a matching surface matched with the locking section of the bone nail. The nail seat may further include the rod clamping arm. The rod clamping arm of the nail seat and the rod clamping arm of the hook seat are respectively located on two sides of the through hole.

Joint surfaces of the hook seat and the nail seat are matched with each other. A contact surface of the two is of a rough structure which is beneficial to improving friction.

A stopper which can constrain the sliding distance of the connecting rod that performs axial sliding under the action of an external force after the degradable gasket is degraded and absorbed is also added to the connecting rod. The stopper is a U-shaped hoop that may be inserted into the connecting rod. One end of the stopper has a stopping screw and a corresponding screw hole that point to the connecting rod to prevent the connecting rod from falling off or displacing.

The sliding clearance between the sliding block and the chute in the axial direction of the bone plate is 0.2 to 1 mm. The thickness of the embedded degradable gasket is 0.2 to 1 mm. The thickness of the laying-type degradable gasket is 0.1 to 0.5 mm. The thickness of the tile-type degradable gasket is 0.2 to 1 mm.

The degradable gasket is made of magnesium or zinc or a composite consisting of magnesium and zinc, or a composite consisting of magnesium and polylactic acid coating externally thereon, or a composite consisting of zinc and polylactic acid coating externally thereon, or a composite consisting of the composite consisting of magnesium and zinc and polylactic acid coating externally thereon that may be degraded in vivo.

The degradable gasket is a complete gasket, or a plurality of layers of gaskets made of the same composite material or a plurality of layers of gaskets made of different composite materials are overlaid to use to control the degradation rate.

The present disclosure has the beneficial effects that: the internal fracture fixation performed by using the bone fixation system capable of gradually changing from rigid fixation to axial non-rigid fixation can achieve rigid fixation in the early period. With the fracture healing and the gradual degradation of a biomaterial, the axial fixation strength will be weakened gradually, the contact between the broken ends of the fracture will be close gradually, and the mutual axial compressive stress between the two broken ends will be gradually increased. When the biomaterial is degraded completely, physiological axial compressive stress not affected by fixation will be obtained between the broken ends of the fracture on the premise of maintaining lateral and rotational stability. Therefore, static fixation does not need to be transformed into dynamic fixation through a secondary surgery before fracture healing, and there is no need to remove an internal fixture after the fracture healing because there is no stress shielding any more. Thus, the fracture fixation quality can be improved, the risks of delayed fracture healing, nonunion, fracture and loosening of internal fixture, and the like can be reduced, the healing can be accelerated, the course of treatment can be shortened, the disability can be reduced, the cost can be reduced, and huge social and economic benefits are produced.

The present disclosure cannot only perform a surgical operation in the same manner as a bridge combined internal fracture fixation device disclosed in CN200510010654.3 that a connecting rod is placed first and then a connecting block is placed on a side of the connecting rod and is fixed by using a bone nail, that is, the surgical operation is performed in a manner of determining the direction of a bridge surface (connecting rod) and suspending the bridge surface at a quasi-fixed position first, and then driving a pile and establishing a bridge pier (implanting a nail), but also perform the surgical operation in a manner different from all existing fixation methods for fixation devices in limbs that a bone nail without a screw head is screwed according to the requirements of fracture fixation first, and then a connecting rod is placed on a side of the bone nail and is fixed by using a compression nut after being connected to a connecting block in a sleeving manner. The bone nail and the connecting block may not be perpendicular to each other, that is, the surgical operation is performed in a manner equivalent to selecting a pile site to establish a bridge pier (implanting a screw) first and then supporting a bridge surface (connecting rod), which is more flexible and free than the former one, and even if the axis of the through hole of the connecting block is located at an edge of a bone, the nail entering direction can also be appropriately adjusted to screw the bone nail into a firmer bone as far as possible, thereby meeting the requirement of fixation for complex comminuted fractures, and can also reduce the operations of bending and shaping the connecting rod.

REFERENCE SIGNS IN THE DRAWINGS

Figure 1:
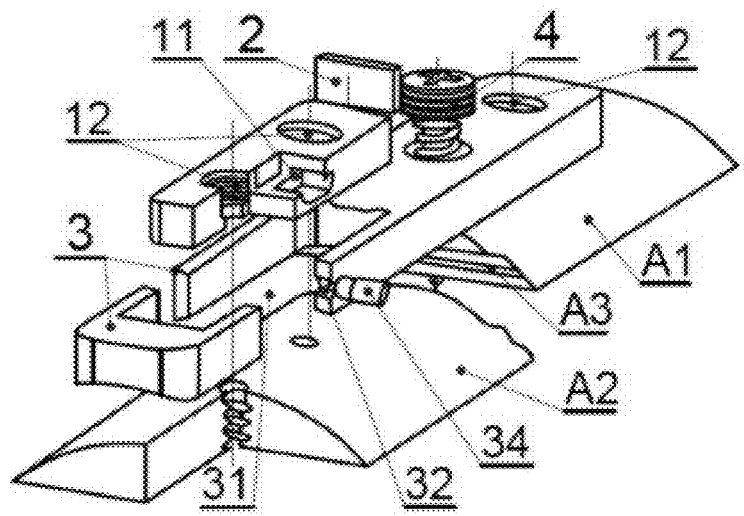
FIG. 1 is a structural effect diagram of a key slot plug-in embedded bone plate of Embodiment 1.

1—sliding block; 1(a)—porous sliding block; 1(b)—single—hole sliding block; 11—key slot; 12—bone nail through hole; 13—side wall; 14—bulge; 15—deformation seam;
2—degradable gasket; 21—embedded degradable gasket; 22—laying-type degradable gasket; 23—tile-type degradable gasket; 20—non-degradable gasket;
3—bone plate; 31—through slot; 32—key pin hole; 33—key pin; 34—inner wall; 35—groove belt; 36—groove; 37—groove bottom surface; 38—through hole;
4—bone nail; 41—implanting section; 42—limiting section; 43—locking section; 44—compression nut; 45—first screwdriver interface; 46—second screwdriver interface; 47—third screwdriver interface; 48—fourth screwdriver interface; 49—nail head; 491—integrated common nail head; 492—combined common nail head; 493—locking nail head;
5—connecting block; 51—block body; 511—through hole; 52—rod clamping arm; 521—rod pressing frame; 522—rod hooping frame; 53—hook seat; 54—nail seat;
6—connecting rod;
7—stopper; 71—stopping screw hole; 72—stopping screw;
a—bone nail swing circle center; b—bone nail swinging angle; c—bone nail horizontal adjustment distance;
A1—distal fracture end; A2—proximal fracture end; and A3—fracture line.

DETAILED DESCRIPTION OF THE EMBODIMENTS

In order to make the technical problems solved by the present application, technical solutions, and beneficial effects clearer, the present disclosure is further described below in detail with reference to embodiments. It should be understood that, in the description of the application of the present disclosure, the terms "left and right", "upper and lower", and the like indicate an orientation or position relationship based on the orientation or position relationship shown in the drawings, "end" refers to an axial edge, "side" refers to a radial edge, "top surface" refers to a surface, facing an operator, of a bone plate, "bottom" refers to a surface opposite to the "top surface", "a proximal end of fracture" and "a distal end of fracture" are bounded by a fracture line, the former refers to a relatively fixed end closer to the a shoulder joint or a hip joint, and the later refers to a relatively free end far away from the abovementioned joints. These terms are only for the convenience of describing the application of the present disclosure, rather than requiring that the application of the present disclosure must be constructed and operated in specific orientations, thus, they cannot be understood as limitations to the present disclosure.

There may be a plurality of implementation manners for implementing bone fixation systems. In summary, the bone fixation systems may be divided into plate-shaped fixation systems and rod-shaped fixation systems according to the shapes and structures of bone bridges. The plate-shaped fixation systems may also be divided into a through slot type and a groove type according to whether a chute penetrates through all layers of a bone plate or not. Correspondingly, the shapes and combination modes of a sliding block and the chute of the through slot are correspondingly divided into an embedded type and a tiled type, that is, the through slot corresponds to the embedded type and the groove corresponds to the tiled type. Further, when the shapes and combination modes of the sliding block and the chute of the through slot are in the embedded type, the embedding manner of the sliding block and the chute may also adopt a plug-in embedded type and a rotary embedded type. Further, the plug-in embedded type combination manner may also be divided into a tenon riveting type and a key slot type.

Specific embodiments are further described below with reference to the drawings. Embodiment 1, Embodiment 2, Embodiment 3, and Embodiment 4 are plate-shaped fixation systems. Embodiment 5 is a rod-shaped fixation system.

Embodiment 1

FIG. 1 is a structural effect diagram of a through slot-type bone plate of a key slot plug-in embedded type structure used for fixation of a single fracture of a backbone of the present disclosure. In the drawing, a distal fracture end A1 is on the right side of a fracture line A3, and a proximal fracture end A2 is on the left side of the A3-fracture line. Bone nail through holes 12, fixing a side of the distal fracture end A1, of a bone plate 3 are locking screw holes without sliding blocks, and the number is not limited to two shown in FIG. 1. The bone plate 3 on a side of the proximal broken end of fracture A2 has a through slot 31. The bone nail through holes 12 are all formed in a sliding block 1 in the through slot 31. The sliding block as shown in FIG. 1 is abbreviated as a porous sliding block (1a) structure with only two bone nail through holes 12, and the bone nail through holes 12 are also locking screw holes. The shape of the sliding block 1 is basically the same as the through slot 31 of the bone plate 3, only the length is slightly shorter than that of the through slot 31, the width is the same as that of the through slot 31, but the sliding block 1 is in clearance fit with the through slot 31. Preferably, the sliding block 1 is 0.2 to 1 mm shorter than the through slot 31, that is, the axial clearance between the sliding block 1 and the through slot 31 is 0.2 to 1 mm, and is used for inlaying an embedded degradable gasket 21 with the same shape and size as those of the clearance. The porous sliding block (1a) has an axially formed key slot 11 on at least one side. A key pin hole 31 is formed in a side wall of the bone plate 3 corresponding to the center of the key slot 11. Preferably, two pairs, namely, four key slots/key pin holes, are formed in both sides of the bone plate 3. After the sliding block 1 is embedded into the through slot 31, key pins 34 are inserted into the key slot 11 through the key pin holes 32, and the key pins 34 are fixed, the sliding block 1 is connected to the bone plate 3 integrally and the sliding block 1 can only perform axial translation in the through slot 31. In order to meet the requirements of fixation of different fractures, preferably, the length of the key slot 11 at least allows the sliding block 1 to translate 1 mm to both ends. The connection manners of the key pins 34 and the key pin holes 32 may be a plurality of forms, such as screwing, riveting, and welding.

The number of the bone nail through holes of the bone plate 3 and the numbers of fixed bone nail through holes 12 and sliding bone nail through holes 12 distributed at both ends of the fracture line may be selected according to a preoperative planning and actual situations during an operation.

It must be emphasized that, during an operation, a clearance between the sliding block 1 and the through slot 31 must be left close to the fracture line A3, so that the axial stress generated by muscle tension and limb activities can obtain a space that can drive the distal fracture end A2 to drive a bone nail 4 and the bone plate 3 fixed thereon to translate to the proximal fracture end A1 by using the clearance recovered after the abovementioned embedded degradable gasket 21 is absorbed, and the contact between the distal fracture end A1 and the proximal fracture end A2 is closer, thereby generating axial compressive stress stimulation conducive to fracture healing between the fracture ends.

Embodiment 2

Figure 2:
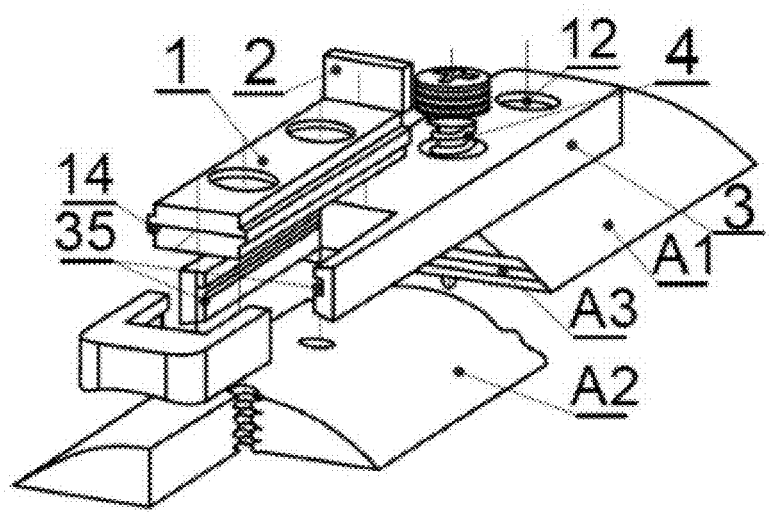
FIG. 2 is a structural effect diagram of a tenon riveting plug-in embedded bone plate of Embodiment 2.

FIG. 2 is a structural effect diagram of a through slot-type bone plate of a tenon riveting plug-in embedded type structure used for fixation of a single fracture of a backbone of the present disclosure. In the drawing, except that the embedding manner of the sliding block 1 and the through slot 31 is changed to a rectangular plug-in tenon riveting structure, the rest are the same as those in Embodiment 1. That is, the rectangular bulges 14 are respectively formed in a left inner wall and a right inner wall of the sliding block 1. Groove belts 35 matched with the bulges 14 are respectively formed in the inner walls on both sides of the through slot 31, so as to form a matched rectangular groove-shaped tenon riveting structure for connecting. The bulges 14 are embedded into the groove belts 35 and may slide in the groove belts 35, so as to limit the sliding block 1 to only perform axial translation movement in the through slot 31.

Figure 3:
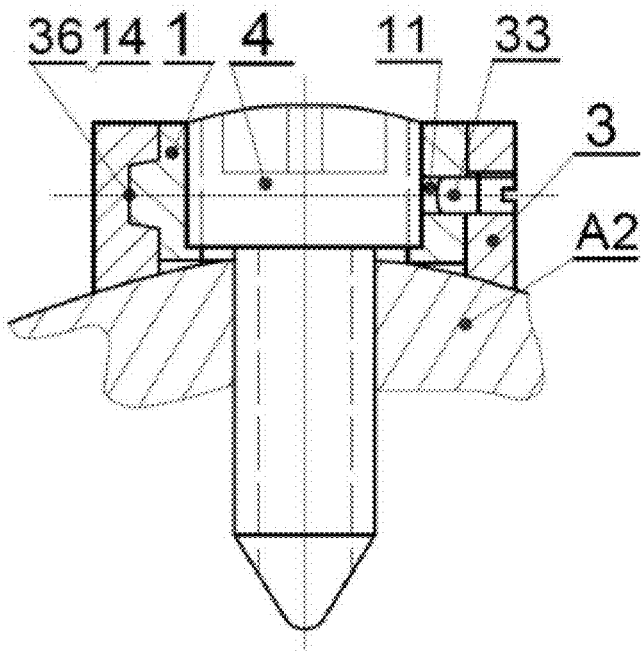
FIG. 3 is a structural two-dimensional diagram of two types of plug-in embedded sliding block/through slot of Embodiment 1 and Embodiment 2.

The tenon riveting structure may also in other forms, such as a dovetail. FIG. 3 is a two-dimensional schematic diagram after a riveting structure on a left side and a key slot/key pin hole structure on a right side of a central line are assembled.

Embodiment 3

Figure 4:
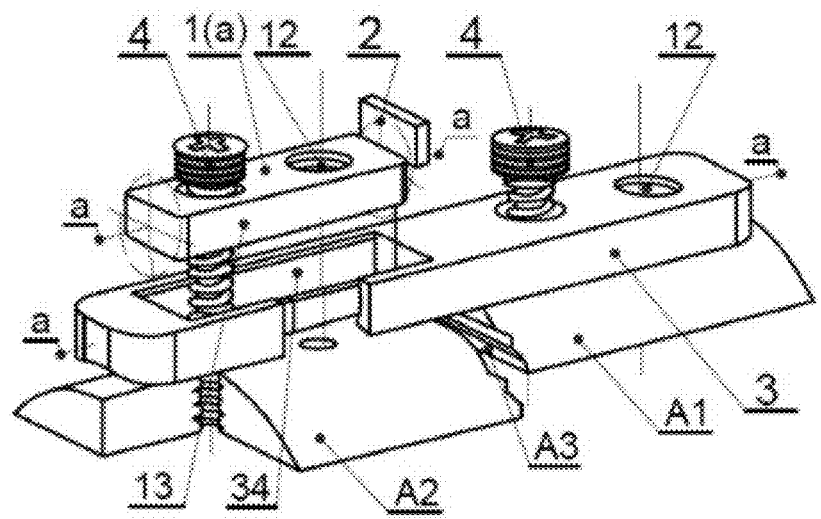
FIG. 4 is a structural effect diagram of a rotary embedded bone plate of Embodiment 3.

FIG. 4 is a structural effect diagram of a through slot-type bone plate of a rotary embedded structure used for fixation of a single fracture of a backbone of the present disclosure. In the drawing, except the embedded structure of the sliding block 1 and the through slot 31, the rest structures are the same as those in Embodiment 1.

Figure 5:
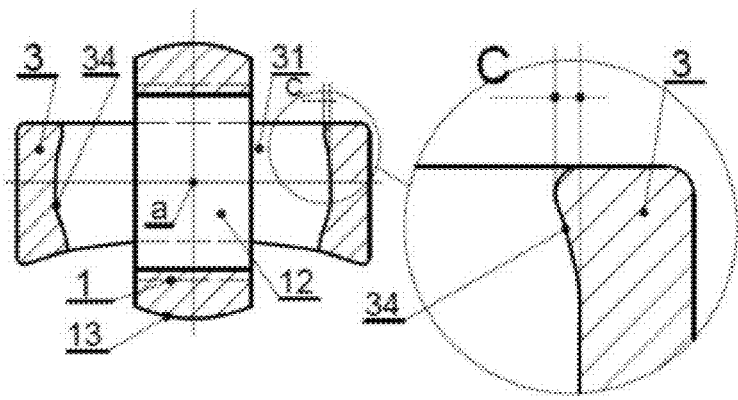
FIG. 5 is a two-dimensional schematic diagram of an assembling process of a rotary embedded sliding block/through slot of Embodiment 3.
Figure 6:
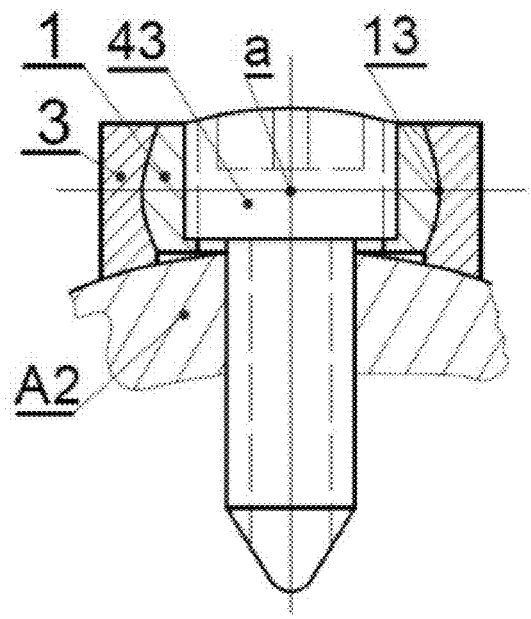
FIG. 6 is a two-dimensional schematic diagram of a locking fit form of the rotary embedded sliding block/through slot of Embodiment 3.

In Embodiment 3, two side walls of the sliding block and two inner walls of the through slot 31 are arranged as symmetrical concentric circles. The sliding block 1 is embedded into the through slot 31 in a rotating manner, as shown in FIG. 5 and FIG. 6. In order to facilitate the rotation of the sliding block 1 into the through slot 3, edges of two sides of the through slot 31 of the bone plate 3 may be chamfered into arc shapes. Thus, firstly, the sliding block 1 may be conveniently rotated into the through slot 31. Secondly, the sliding block 1 may rotate transversely by taking a longitudinal axis of the bone plate 3 as a rotating axis in a fixing process, so that included angles between the axes of the bone nail through holes 2 in the sliding block 1 and a vertical axis of a surface of the bone plate are adjusted steplessly, and the bone nail 4 penetrates through the nail plate 3 conveniently at an inclined angle to find a thicker and firmer bone for screwing in. Therefore, the fixation strength can be enhanced better, and a cross nail distribution structure which is more resistant to external force of loosening and pulling the nail is formed. Thirdly, the inclusiveness of the chute 31 to the slide block 1 is not destroyed, so that the sliding block 1 cannot disengage from the through slot 31 under any external force except the same rotation mechanism as that when the sliding block is embedded into the through slot 31. After the bone nail 4 that penetrates through the bone nail through holes 12 in the sliding block 1 and is fixed to the interior of the bone, the sliding block 1 extruded by the bone nail 4 can still extrude the through slot, so that the sliding block 1 and the through slot 31 are connected integrally to form a complete bone plate 3.

Figure 7:
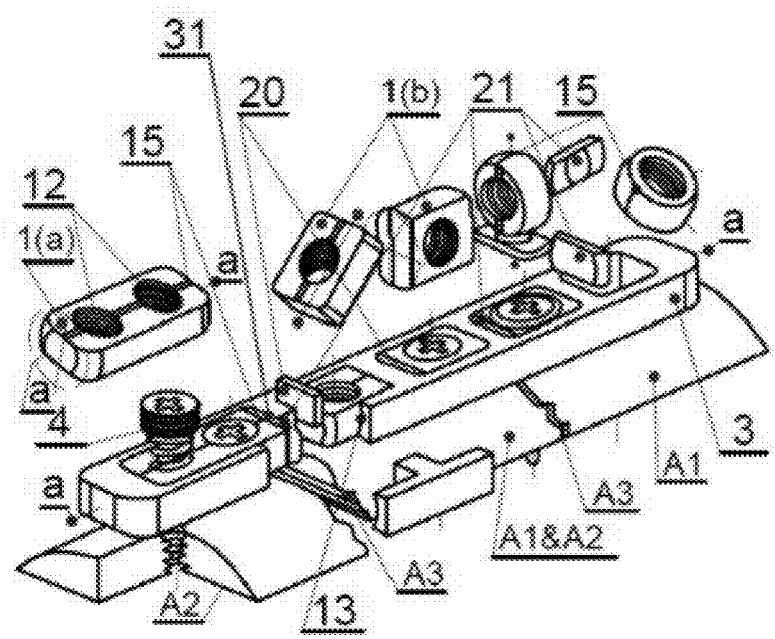
FIG. 7 is structural effect diagram of a plurality of rotary embedded sliding blocks and fixation thereof in two fractures of Embodiment 3.

In order to facilitate the rotation of the sliding block 1 into the through slot 31, a deformation seam 15 that longitudinally penetrates through all layers of the sliding block 1 may also be formed in a side wall of one end of a single-pore sliding block 1(b) in the axial direction of the bone plate 3, so that closed bone nail through holes 12 in the sliding block 1 change into open bone nail through holes 12. The side wall at the other end symmetrical with the side wall, provided with the deformation seam 15, of the sliding block 1 is of a complete side wall structure, or an incomplete side wall structure provided with a crack that is formed from shallow to deep or from an inner edge to an outer edge and does not penetrate through the side wall, so that the sliding block 1 has a transverse elastic deformation condition. Both ends of the porous sliding block 1(a) are the same or similar to the structure of the single-pore sliding block 1(b), but all side walls between all bone nail through holes 12 in the whole porous sliding block 1(a) are all provided with deformation joints (5) in the axial direction, so that the continuity of both sides of the whole sliding block 1 is maintained only by the complete side wall at one end or the remaining part of the side wall. FIG. 7 shows structures of a plurality of sliding blocks 1 of Embodiment 3.

FIG. 7 further illustrates key points of placement of the embedded gasket 21 when two fractures of a backbone are fixed. Firstly, all bone nail through holes 12 at the distal fracture end A2 and the proximal fracture end A1 need to be formed in the sliding block 1, and all embedded degradable gaskets 21 need to be placed at one end, close to the fracture line A3, in the through slot 31. Secondly, all bone nail through holes 12 in a free bone section in the middle of the fracture cannot slide. If the bone nail through holes 12 in the bone plate corresponding to the free bone section are formed in the sliding block 1 rather than directly being formed in the bone plate, then the degradable gasket 20 with the same shape and size is embedded into a clearance, so as to eliminate the clearance, and enhance the rigidity between the sliding block 1 and the bone plate 3.

Figure 8:
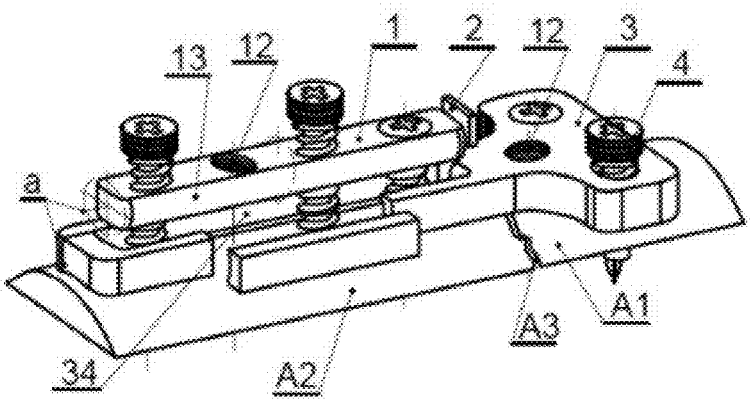
FIG. 8 is a structural effect diagram of fixing bone end fractures of Embodiment 3.

FIG. 8 is a structural effect diagram of Embodiment 3 of the present disclosure applied to fixation of a bone end fracture. In the drawing, A represents a backbone of a tubular bone, and is located at a proximal end of the fracture line; A1 represents a metaphysis proximal to a joint of the tubular bone, such as a distal radius, and is located at a distal end of the fracture. The bone nail through holes 12 fixing a side of A1 are also locking screw holes without sliding blocks. However, the bone nail through holes 12 can only be arranged transversely, and correspondingly, the bone plate 3 at the fracture end can only be widened transversely, so that the whole bone plate 3 becomes a "T" shape or an "L" shape.

Embodiment 4

Figure 9:
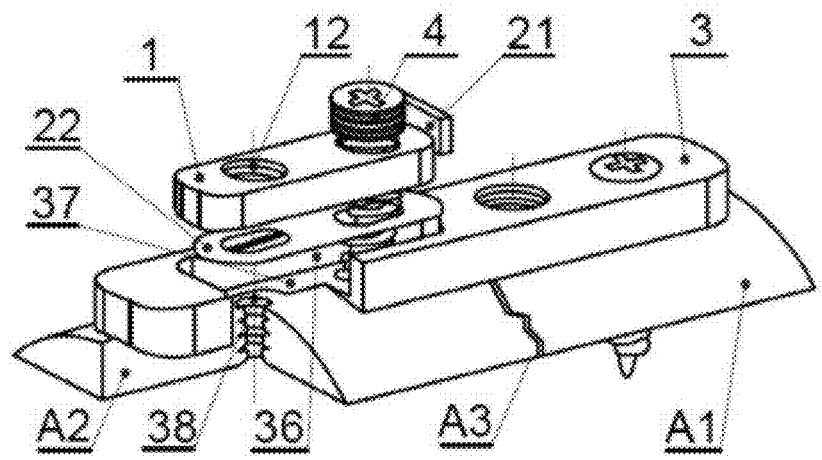
FIG. 9 is an assembling effect diagram of a tiled groove-type bone plate of Embodiment 4.
Figure 10:
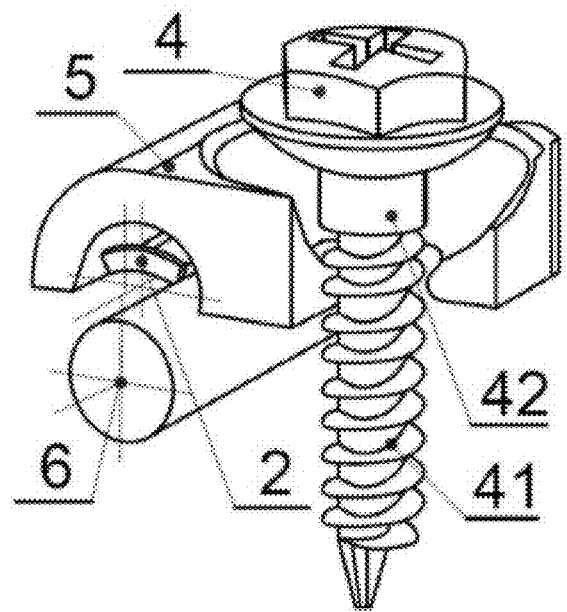
FIG. 10 is a structural decomposition effect diagram of an integrated common nail head and a single-rod clamping arm pressing rod of Embodiment 5.
Figure 11:
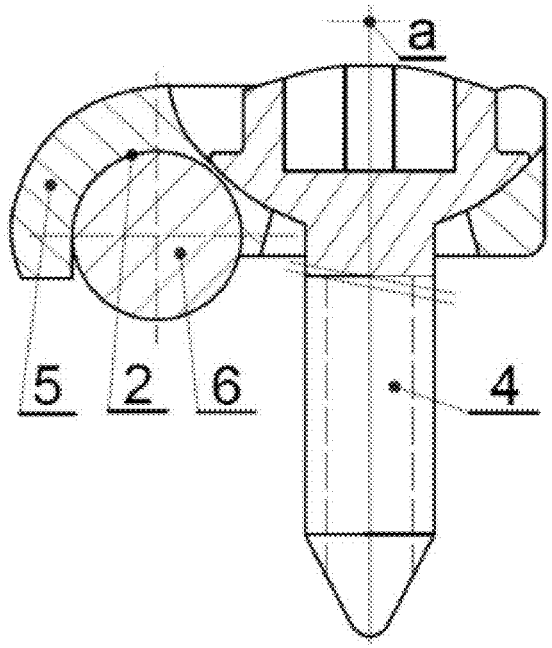
FIG. 11 is a structural two-dimensional diagram of the integrated common nail head and the single-rod clamping arm pressing rod of Embodiment 5.
Figure 12:
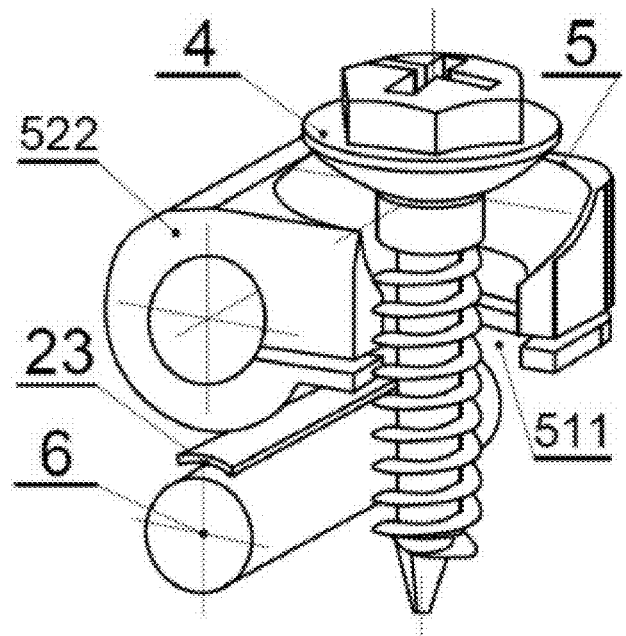
FIG. 12 is a structural decomposition schematic diagram of the integrated common nail head and a single-rod clamping arm hoop rod of Embodiment 5.
Figure 13:
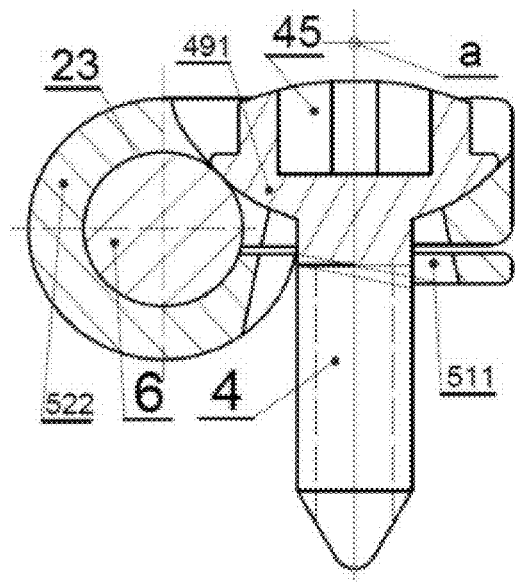
FIG. 13 is a structural two-dimensional diagram of an integrated common nail head and the single-clamping arm hoop rod of Embodiment 5.
Figure 14:
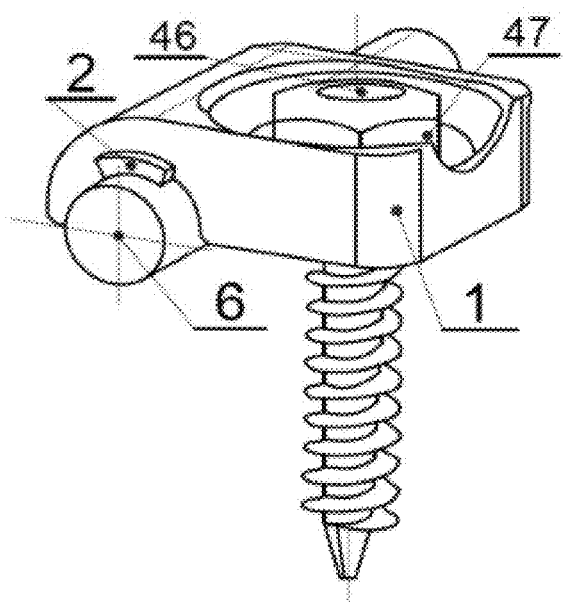
FIG. 14 is a structural effect diagram of a combined common nail head and the single-rod clamping arm pressing rod of Embodiment 5.
Figure 15:
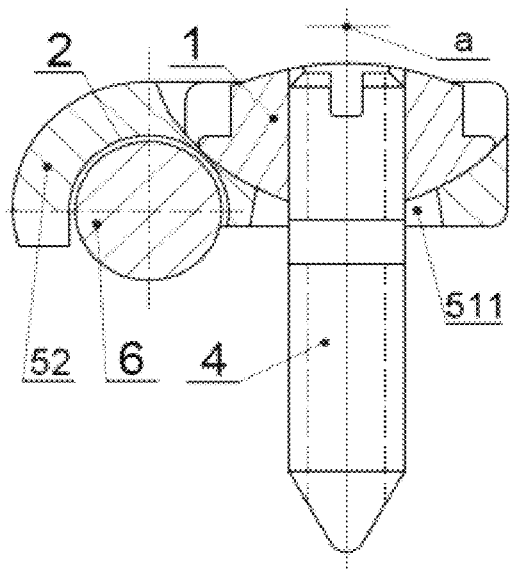
FIG. 15 is a structural two-dimensional diagram of the combined common nail head and the single-rod clamping arm pressing rod of Embodiment 5.
Figure 16:
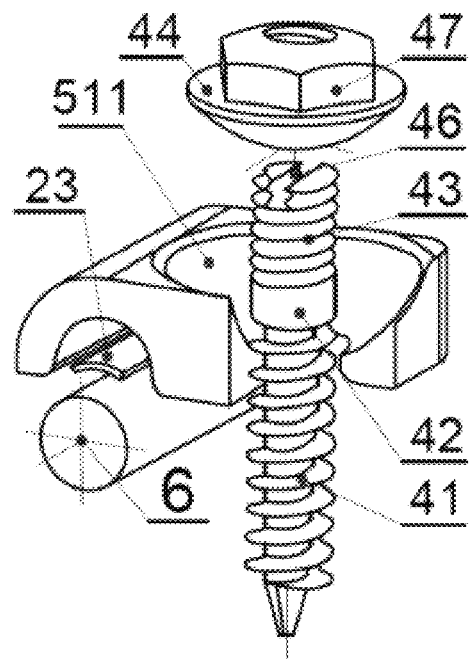
FIG. 16 is a structural decomposition effect diagram of the combined common nail head and the single-rod clamping arm pressing rod of Embodiment 5.
Figure 17:
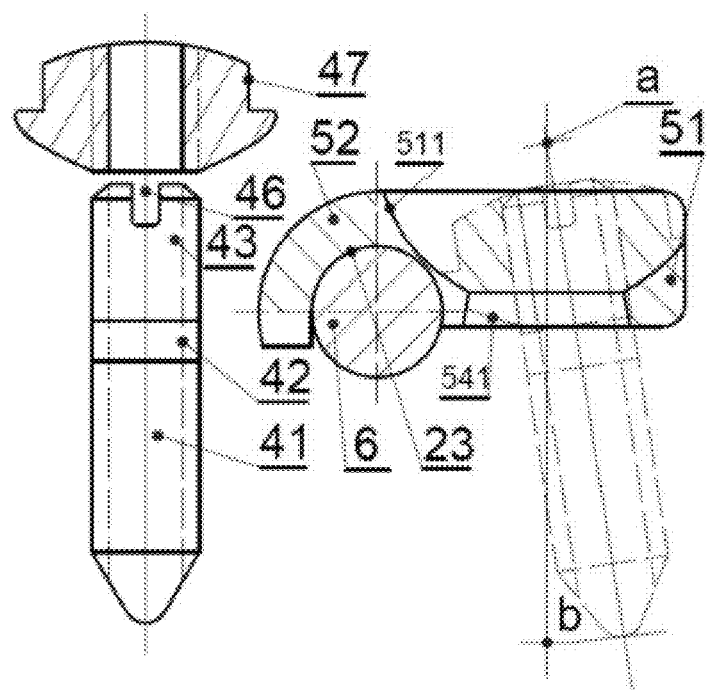
FIG. 17 is a structural decomposition and working principle schematic diagram of the combined common nail head and the single-rod clamping arm pressing rod of Embodiment 5.

FIG. 9 is a structural effect diagram of a tiled through slot-type bone plate used for fixation of fracture of a backbone of the present disclosure. In the drawing, except the structures of the sliding block 1 and the chute, the rest structures are the same as those in Embodiment 1.

In FIG. 9, the chute in the left side of the bone plate 3 is formed as a groove 36 that is located in a top surface of the bone plate 3 and does not penetrate through all layers of the bone plate 3. The width of the groove 36 is greater than the diameter of the bone nail 4. A through hole 38 that may be used for the bone nail 4 to penetrate through is formed in the center of a groove bottom surface 37. The size and the shape of the through hole 38 allow the bone nail 4 of the sliding block 1 to move in the axial direction of the bone plate 3. The shape of the sliding block 1 is basically the same as that of the groove 36, only the length is slightly shorter than the groove 36, the width is the same as that of the through slot 31, but the sliding block 1 is in clearance fit with the through slot 31. The sizes and the positions of the bone nail through holes 12 in the sliding block 1 also correspond to those of the through holes 38 in the groove 36, and can be tiled in the groove 36. Preferably, the sliding block 1 is 0.2 to 1 mm shorter than the groove 36, that is, the axial clearance between the sliding block 1 and the groove 36 is 0.2 to 1 mm, and an embedded degradable gasket 21 with the same shape and size as those of the clearance may be embedded into one end, close to the fracture line A3, of the sliding block 1.

In Embodiment 4, a laying-type degradable gasket 22 which has the shape and the size matched with those of the groove bottom 37 and the thickness of less than 1 mm may also be laid between the sliding block 1 and the groove 36, so as to eliminate micro-motion between the sliding block 1 and the groove 36, and form a clearance that cannot hinder the sliding of the sliding block 1 and the groove 36 and does not cause transverse rotation and micro-motion of the sliding block 1 after the laying-type degradable gasket 22 is degraded and absorbed.

As shown in FIG. 9, the bone plate 3 using a laying-type sliding block may use the embedded degradable gasket 21 and the laying-type degradable gasket 22 at the same time.

Embodiment 5

Embodiment 5 illustrates a rod-shaped fixation system, which consists of a connecting rod 6, a connecting block 5, a bone nail 4, and a degradable gasket 2 that may be added together.

As shown in FIG. 10 to FIG. 19, the connecting rod 6 is round rod-shaped. Preferably, the overall length of the round rod is equal in diameter. An outer surface of the connecting rod 6 is smooth, or is a knurled surface such as straight lines and mesh lines.

The connecting block 5 consists of a block body 51 and a rod clamping arm 52 connected integrally. The block body 51 is flat, and a through hole 511 for a bone nail implanting section 41 to penetrate through is formed in the middle. The through hole 511 of the connecting block 5 is a smooth hole or a screw hole. The shape of the smooth hole may be a cylindrical surface, a frustum cone-like surface, a spherical surface, or the like.

As shown in any drawing of FIG. 10 to FIG. 17, preferably, when the through hole 51 is a smooth hole, a pore channel is divided into an upper part and a lower part. The upper part is a spherical surface with a large upper part and a small lower part, so as to be matched with a lower end face, representing a spherical surface, of a compression nut 44 in screw thread fit with the bone nail locking section 43. The lower part is a conical surface with a large upper part and a small lower part. The diameter of the bone nail implanting section 41 is smaller than the minimum diameter of the through hole 511. The bone nail implanting section 41 may swing conically within a scope constrained by the conical surface of the through hole.

Figure 18:
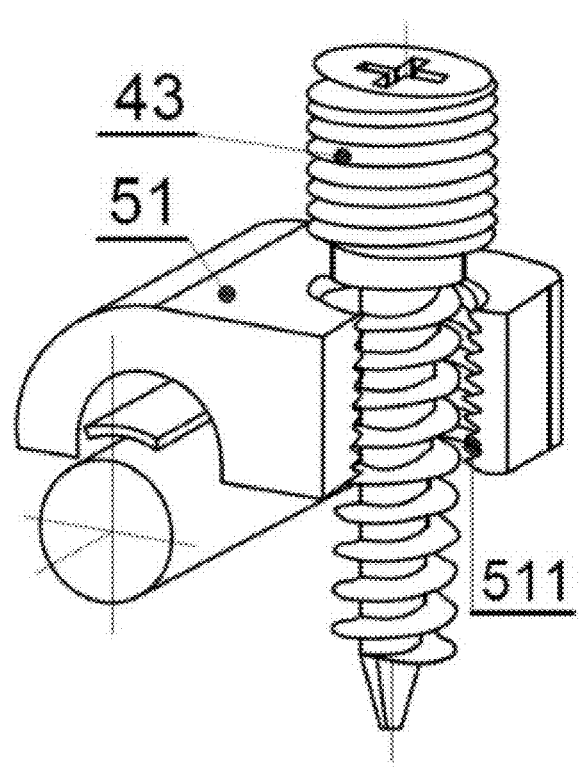
FIG. 18 is a structural decomposition effect diagram of a locking nail head and the single-rod clamping arm pressing rod of Embodiment 5.
Figure 19:
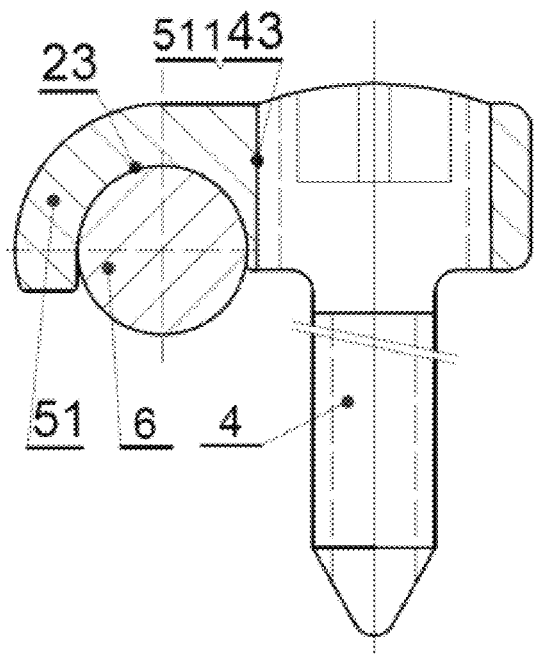
FIG. 19 is a structural two-dimensional diagram of the locking nail head and the single-rod clamping arm pressing rod in Embodiment 5.

As shown in FIG. 18 and FIG. 19, the through hole 511 of the connecting block 5 is a screw hole. The screw hole may be straight, may also be conical, or may also be a single-start screw threads or double-start screw threads. At this time, a screw thread pair is formed in the locking section 43 of the bone nail, and the leads of the screw threads of the implanting section 41 and the locking section 43 of the bone nail are consistent.

Figure 20:
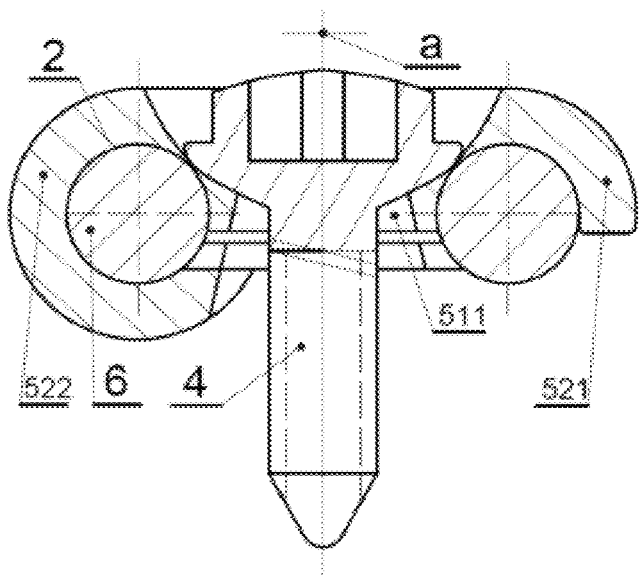
FIG. 20 is a structural two-dimensional schematic diagram of the integrated common nail head and a dual-rod clamping arm hoop rod and pressing rod in Embodiment 5.
Figure 21:
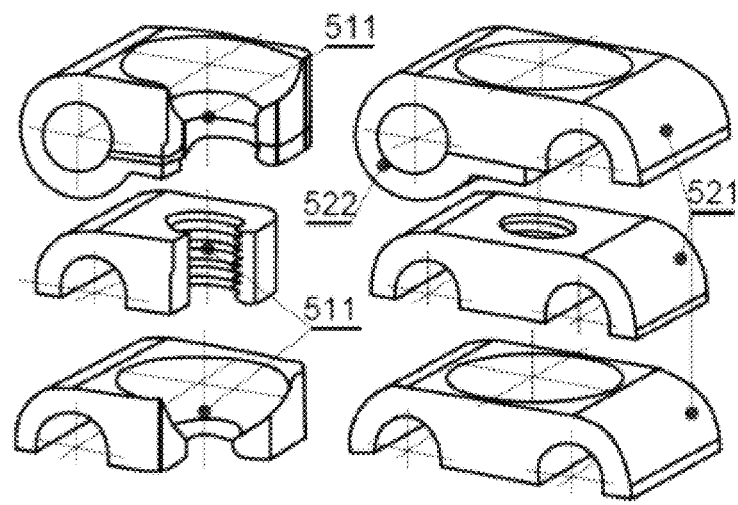
FIG. 21 is a structural schematic diagram of part different nail heads and connecting blocks of rod clamping arm structures in Embodiment 5.

As shown in FIG. 20 and FIG. 21, further, one side or symmetrical two sides of the block body 51 is connected the rod clamping arm 52. The fixing manner of the rod clamping arm 52 to the connecting rod 6 is divided into two types: a rigid pressing rod and an elastic hoop rod. An end face of the rod clamping arm 52 of the rigid pressing rod is free, and a surface, fitting the bone, of the rigid pressing rod is sunken to form a rod pressing frame 521. An inner surface of the rod pressing frame 521 is a small arc surface, a semicircular arc surface, or a U-shaped surface. The radius of the arc surface is equal to the radius of the connecting rod 6. The rod pressing frame 521 forms a semi-enclosed state for the connecting rod 6, and can only fix the connecting rod 6 by clamping together with a bone surface. The rod clamping arm 52 of the elastic hoop rod is a rod hooping frame 522, that is, an end face of the rigid rod pressing arm extends around the surface of the connecting rod 6 and a lower surface of the block body 5, so as to form a fully-enclosed state resembling a slotted tube for the connecting rod 6. A smooth through hole 511 is formed at a projection of the through hole of the block body 51, so as to fix the connecting rod 6 in a manner of an elastic hoop similar to a hoop. Through this structure, the connecting rod 6 that fails to be in tight fit with the bone surface can be fixed rigidly. In order to only form a clearance in a pressing direction, that is, coaxial or nearly coaxial with the bone nail 4 after the tile-type degradable gasket 23 between the rod hooping frame 522 and the connecting rod 6 is degraded and absorbed, the width of an upper arc surface and a lower arc surface of the rod hooping frame 522 should be set to form clearance fit with the connecting rod 6 after hooping.

Further, the rod clamping arm 52 of the connecting block 5 is adjacent to the through hole 511. The axes of the rod clamping arm 52 and the through hole 511 are perpendicular or nearly perpendicular to each other but do not intersect. There is one rod clamping arm 52, or two rod clamping arms 52 respectively located on two sides of the through hole 511. The connecting block 5 with rod clamping arms 52 may clamp two parallel connecting rods 6, so as to enhance a fixing action on the fracture.

Further, the connecting block 5 may use five structural types: a single rod pressing type, a single rod hooping type, a dual-rod pressing type, a dual-rod hooping type, and a rod pressing and hooping combined type. The through hole 511 of each structure type may also be divided into two hole types: a smooth hole type and a screw hole type, which are respectively matched with the under-mentioned three types of bone nails 4.

Figure 22:
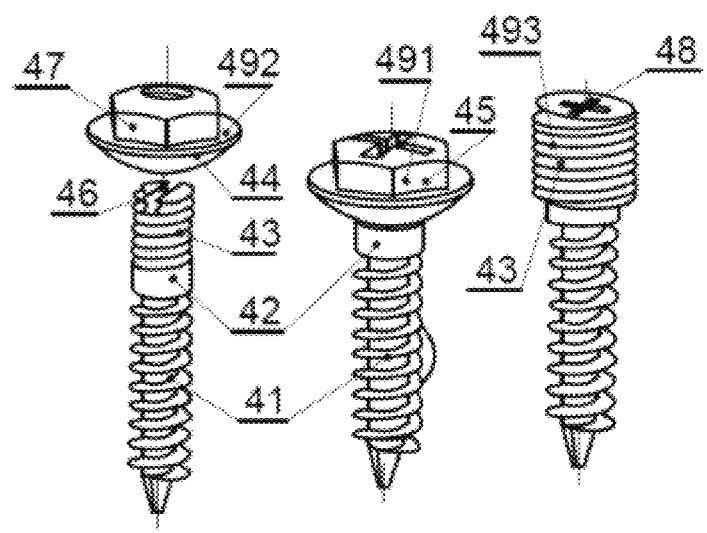
FIG. 22 is a structural schematic diagram of bone nails with different nail head structures in Embodiment 5.
Figure 23:
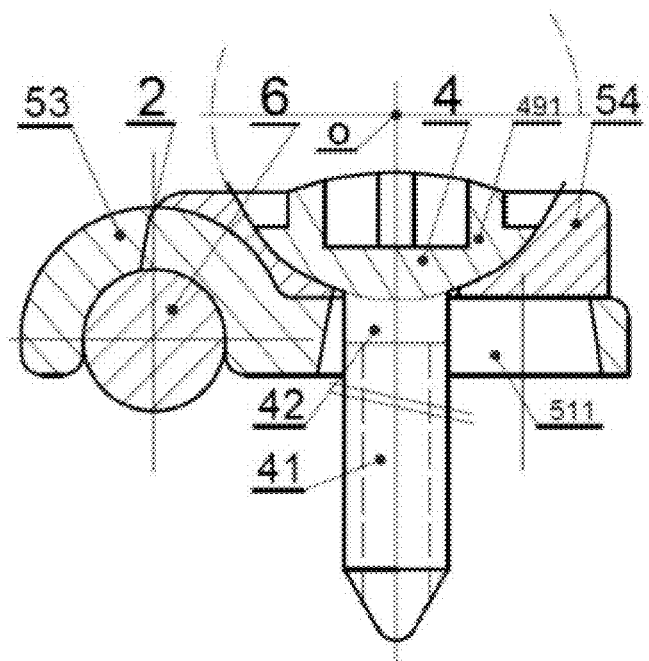
FIG. 23 is a structural two-dimensional schematic diagram of the integrated common nail head and a combined connecting block and single-rod clamping arm pressing rod of Embodiment 5.
Figure 24:
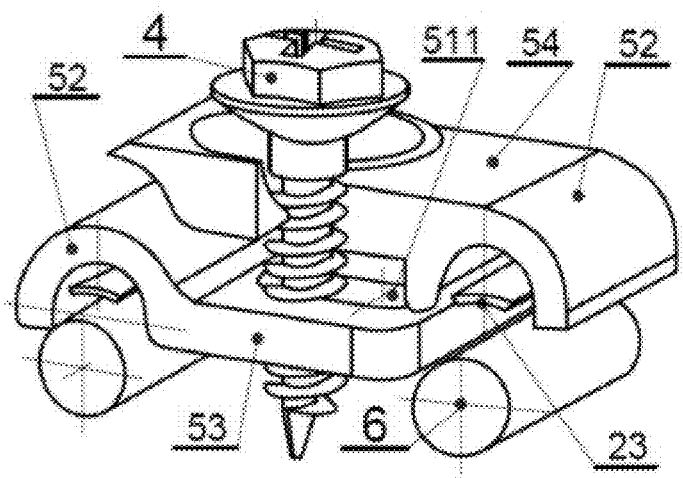
FIG. 24 is a structural decomposition effect diagram of the integrated common nail head and the combined connecting block and single-rod clamping arm pressing rod of Embodiment 5.
Figure 25:
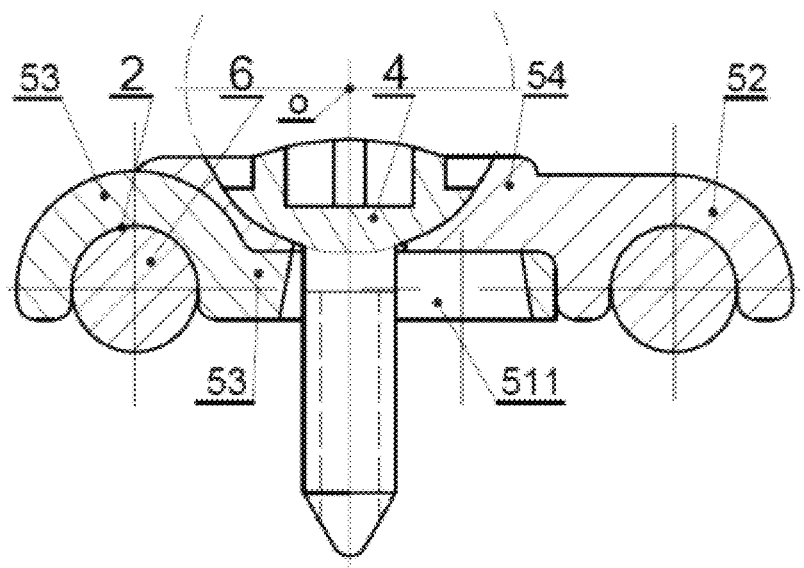
FIG. 25 is a structural two-dimensional schematic diagram of the integrated common nail head and the combined connecting block and single-rod clamping arm pressing rod of Embodiment 5.
Figure 26:
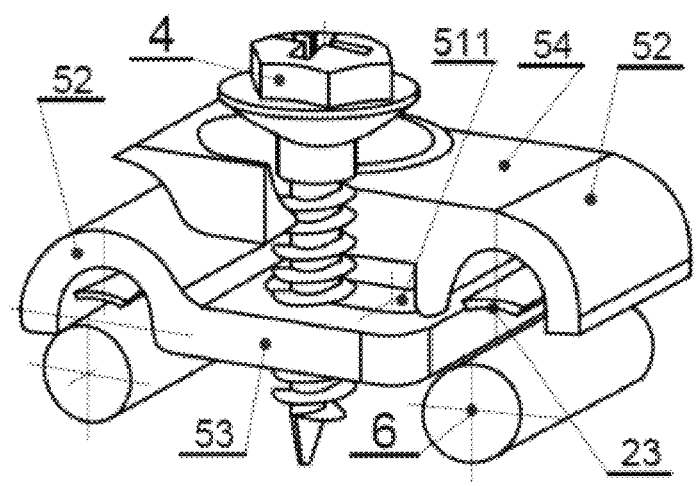
FIG. 26 is a structural decomposition effect diagram of the integrated common nail head and the combined connecting block and single-rod clamping arm pressing rod of Embodiment 5.
Figure 27:
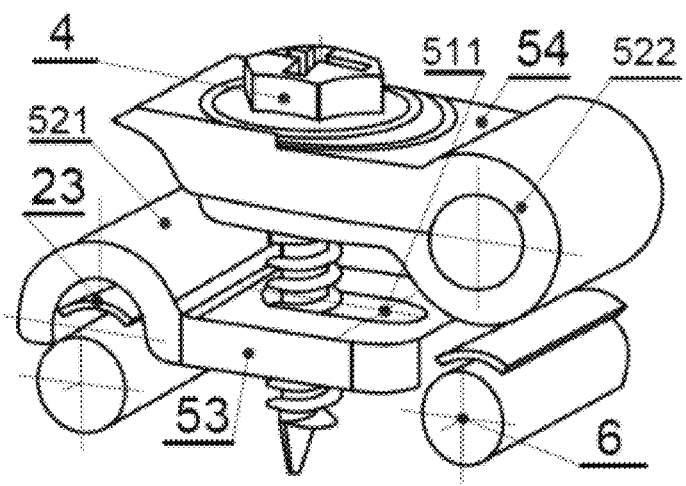
FIG. 27 is a structural decomposition effect diagram of the combined common nail head and the combined connecting block and single-rod clamping arm pressing rod of Embodiment 5.
Figure 28:
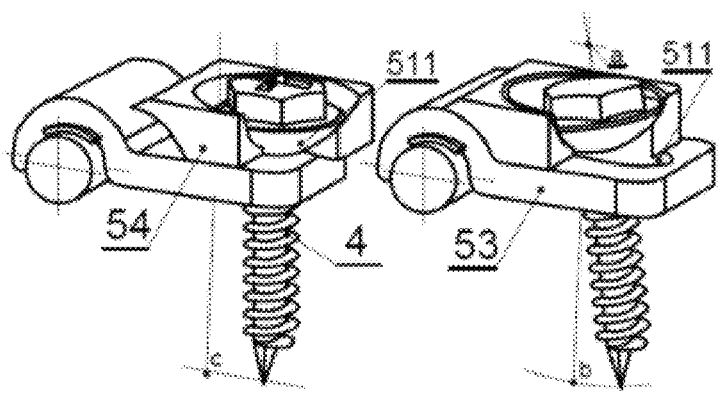
FIG. 28 is an effect schematic diagram of a variable center distance and a swinging angle of the common nail head in a combined connecting block.

As shown in FIG. 22, the bone nail 4 consists of a front implanting section 41 and a rear locking section 43. The implanting section 41 is preferably in a bone screw thread shape, and may be implanted into a bone. The locking section 43 is connected to the connecting block 5.

The locking section 43 has three structural types.

As shown in FIG. 10 to FIG. 13, a first structure of the locking section 43 is an integrated common nail head 491 which has a screwdriver interface 45 at a rear end and is larger than the minimum diameter of the smooth through hole of the connecting block 5. The integrated common nail head 491 has a lower spherical surface matched with the upper spherical surface of the through hole 511.

As shown in FIG. 14 to FIG. 17, a second structure of the locking section 43 is a combined common nail head 492 which consists of a threaded rod provided with a second screwdriver interface 46 at a rear end face and a compression nut 44 which is matched with the threaded rod and has a shape similar to that of the integrated common nail head 491. The compression nut 44 has a lower surface matched with the lower spherical surface of the through hole 511 of the connecting block 5, and has a third screwdriver interface 47. The bone nail 4 of this structure is also provided with a smooth rod limiting section 42 with the diameter equal to the major diameter of the implanting section 41 between the locking section 43 and the implanting section 41, so as to limit the depth of the bone nail 4 implanting into the bone. The combined common nail head 492 has the same shape and function as the integrated common nail head 491 has the same shape and function, but the bone nail 4 may be implanted first, and then the positions of the connecting rod 6 and the connecting block 5 are determined according to the position of the bone nail 4 and the axial direction.

As shown in FIG. 18 to FIG. 19, a third structure of the locking section 43 is a locking nail head 493 with a fourth screwdriver interface 48 at a rear end surface matched with a screw hole 13 of the connecting block 5.

Therefore, 15 types of combinations formed by different types of connecting blocks 5 and bone nails may be flexibly applied to fracture fixation according to intraoperative requirements, so as to form a plurality of types of embodiments. FIG. 20 and FIG. 21 illustrate embodiments of partial combinations.

Further, the connecting block 5 may also be formed by overlapping a hook seat 53 and a nail seat 54, as shown in FIG. 23 to FIG. 28. The hook seat 53 forms a lower half part of the connecting block 5. The nail seat 54 forms an upper half part of the connecting block 5. Joint surfaces of the hook seat 53 and the nail seat 54 are matched with each other, and a contact surface of the two is of a rough structure which is beneficial to improving friction. The seat 53 has the rod clamping arm 52 and the lower half part of the through hole 511. The through hole 511 of the hook seat 53 has a circular or ellipse-like shape through which the nail body of the bone nail 4 can penetrate. The nail seat 54 has an upper half part of the through hole 511. The through hole 511 of the nail seat 54 has a matching surface, such as a cylindrical surface and a frustum cone-like surface, preferably, a spherical surface or a screw thread pair, matched with the nail head or the locking section of the bone nail 4. The nail seat 54 may also have the rod clamping arm 52. The rod clamping arm 52 of the nail seat 54 and the rod clamping arm 52 of the hook seat 53 are respectively located on two sides of the through hole 511. Preferably, the rod clamping arm 52 connected to the hook seat 53 is in a rod pressing type. The rod clamping arm 52 connected to the nail seat 54 is in a rod hooping type. The spliced connecting block 5 is more convenient to adjust the fixing position and direction of the bone nail 4, and can better adapt to complex and changeable clinical situations. The combinations of the present disclosure are also enriched.

Figure 29:
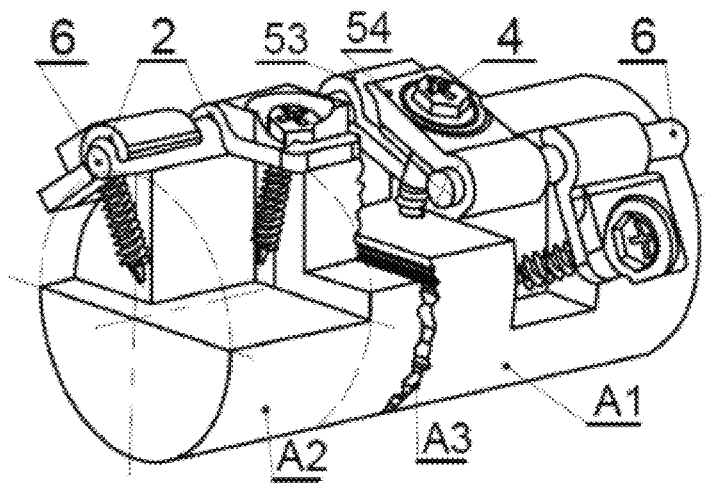
FIG. 29 is an effect schematic diagram of a fixing manner and an axial sliding working mechanism of Embodiment 5.

Taking FIG. 29 as an example, a working mechanism of the present embodiment is described below.

The connecting rod 6 is fixed to a fractured bone by enabling the plurality of bone nails 4 to penetrate through the through holes 511 in the connecting block 5, so that the bone nails 4, the connecting block 5, the connecting rod, and two fracture ends A1 and A2 on two sides of the fracture line A3 may be connected into a rigid fracture/fixture complex.

The same number of bone nails 4 penetrate through the through holes 511 in the connecting block 5 one by one and are screwed into a bone, and the bone nails are screwed tightly, so that the connecting rod 6 and a fractured bone A1 and a fractured bone A2 may be connected into a rigid fracture/fixture complex through the connecting block 5 and the bone nails 4. In order to realize automatic transformation from initial rigid fixation to axial non-rigid fixation of fracture fixation, the present disclosure adopts a manner that the degradable gasket 2 made of a rigid degradable biomaterial is embedded between the connecting block 5 and the connecting rod 6, as shown in FIG. 10, FIG. 12, FIG. 14, FIG. 16, FIG. 18, and FIG. 24. The degradable gasket 2 is a tile-type degradable gasket 23 like a tile shape, and is padded between the rod clamping arm 52 and the connecting rod 6. The cross section of the degradable gasket 2 is a shallow arc smaller than a semicircle. Further, the tile-type degradable gasket 23 may be set as a shape with two ends or one end slightly longer than the connecting block 5 and is folded upward, so as to facilitate installation and increase the using amount of a degradable metal, thereby forming a more concentrated metal ion micro-environment which is beneficial to the bacteria inhibition and inflammation of fracture ends, bone healing, and the like.

After the shown tile-type degradable gaskets 23 are embedded between all connecting blocks 5 and the connecting rod 6 located at the proximal fracture end A2, the connecting blocks 5, the connecting rod 6, the bone nails 4 and the fractured bone still form a rigidly connected fracture/fixture complex at initial fixation. The whole nail-rod system still form stable static fixation at the initial fixation, and the fracture/fixture complex is still of a stable rigid structure. After the tile-type degradable gasket 23 is gradually degraded and absorbed in vivo, a clearance gradually appears between all connecting blocks 5 and the connecting rod 6 on a side of the proximal fracture end A2, and the connection between the connecting blocks 5 and the connecting rod 6 also loosens gradually therewith. However, the position relationship between the bone nails 4 and the proximal fracture end A2 is still of a rigid invariant. Only the combinations between the connecting blocks 5 and the connecting rod 6 become clearance fit. The connecting blocks 5 of which the positions are limited by the bone nails 4 can also only perform axial sliding along the connecting rod 6, that is, the connecting blocks 5 and the connecting rod 6 become axial non-rigid connection. The fixation of the whole nail-rod system is also gradually changed into axial non-rigid dynamic fixation.

During an operation, the connecting rod 6 is placed across the fracture line A3 on the surfaces of the distal fracture end A1 and the proximal fracture end A2, and at least two connecting blocks 5 are distributed at the fracture end of each side appropriately. The connecting blocks 5 fixed to the distal fracture end A1 directly connect and fix the connecting rod 6, the tile-type degradable gaskets 23 are padded between the connecting blocks 5 fixed to the proximal fracture end A2 and the connecting rod 6, and the bone nails 4 penetrating through the connecting blocks 5 at the proximal fracture end added with the tile-type degradable gaskets 23 must to be distributed on both sides of the connecting rod 6 in a staggered manner as far as possible. Thus, after the tile-type degradable gaskets 23 are degraded and absorbed, pressurized contact between the circular connecting rod 6 and the arc-shaped bone surface in linear contact becomes relaxed contact, and the connecting rod 6 may perform axial sliding to a side of the proximal fracture end A2 together with the distal fracture end A1 which is close to the proximal fracture end A2 under the action of an external force. The clearances formed between more than two connecting blocks 5 fixed to the proximal fracture end A2 and the connecting rod 6 are respectively located at different positions of the cross section of the connecting rod 6. Although the connecting rod 6 has lost the radial compression exerted by the connecting blocks 5 at this time, and radial micro-motion can be obtained in the same direction as the pressure, constraint is generated between the connecting blocks 5 and the connecting rod 6 because more than two connecting blocks 5 on the same proximal fracture end A2 allow the directions of the radial micro-motion of the connecting rod 6 to be in different directions. Therefore, there is no radial micro-motion which is not beneficial to the fracture healing between fracture ends A2 and A1.

Figure 30:
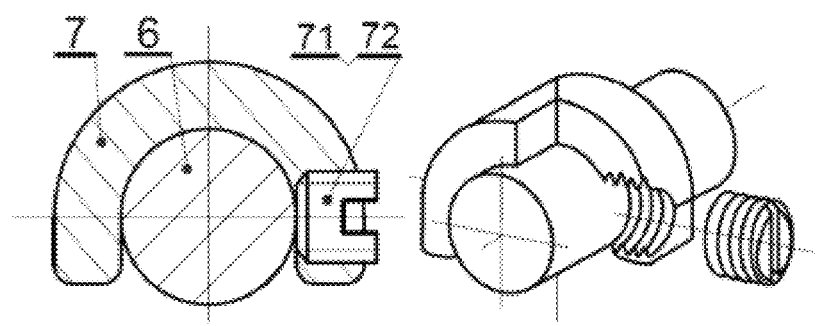
FIG. 30 is a two-dimensional and structural schematic diagram of a stopper in Embodiment 5.

As shown in FIG. 30, in order to prevent instable fractures, such as an oblique fracture or a comminuted fracture, from axial sliding exceeding the range of 1 mm which is not beneficial to the bone healing, the present disclosure also designs a stopper 7 for limiting the moving amplitude of the connecting rod 6. Preferably, the stopper 7 is a U-shaped hoop that can be inserted into the connecting rod 6. The width of a U-shaped opening is greater than or equal to the diameter of the connecting rod 6. A side wall of a free end of the stopper 7 has a stopping screw 71 and a corresponding screw hole 71 that point to the connecting rod 6 to prevent the connecting rod 6 from falling off or displacing. The stopper 7 is clamped on the connecting rod 6, and the connecting rod 6 is tightly pressed by enabling the stopping screw 72 to penetrate through the stopping screw hole 71, so that the stopper 7 may be fixed to the connecting rod 6. When the stopper 7 performs axial movement together with the connecting rod 6 to collide with the connecting rod 5, the connecting rod 6 can be prevented from continuing to move in the direction. The unidirectional axial movement of the whole fracture/fixture complex to the other side can be limited by only installing the stopper 7 on one side of the connecting block 5 added with the tile-type degradable gasket 3, and the axial moving amplitude thereof can be preset. For example, the stopper 7 is additionally installed at each of the two sides of the connecting block 5, the axial movement of the whole fracture/fixture complex to the two sides can be limited, and the axial moving amplitude thereof can be preset.

The degradable gasket 2 described in the above-mentioned Embodiments 1 to 5 of the present disclosure is made of magnesium or zinc or a composite consisting of magnesium and zinc, or a composite consisting of magnesium and polylactic acid coating externally thereon, or a composite consisting of zinc and polylactic acid coating externally thereon, or a composite consisting of the composite consisting of magnesium and zinc and polylactic acid coating externally thereon that may be degraded in vivo. The degradable gasket may be a complete gasket, or a plurality of layers of gaskets made of the same composite material or different composite materials may be overlapped for use, so as to reduce the degradation rate.

The above-mentioned embodiments are preferred embodiments of the application of the present disclosure and are not exhaustive of other embodiments. Therefore, any modifications, equivalent replacements, improvements, and the like made by using the contents of the description and drawings disclosed by the application of the present disclosure shall fall within the scope of protection of the application of the present disclosure.

The embodiments disclosed by the present disclosure are better embodiments, but are not limited thereto. Those of ordinary skill in the art understand the spirit of the present disclosure very easily and make different extensions and changes according to the above-mentioned embodiments, which fall within the scope of protection of the present disclosure as long as not deviating from the spirit of the present disclosure.

What is claimed is:

1. A bone fixation system capable of gradually changing from rigid fixation to axial non-rigid fixation, the bone fixation system comprising:
   a bone bridge that is attached with a connecting piece and realizes fixation through a plurality of bone nails, wherein the bone bridge spans fracture ends of a bone and is configured to be placed on bone surfaces on both sides of the fracture; a first bone nail at one of the fracture ends is configured to fix the bone to the bone bridge directly or through the connecting piece; a second bone nail at the other of the fracture ends is configured to fix the bone to the bone bridge through the connecting piece;
   a degradable gasket made of a rigid degradable biological material is disposed between the connecting piece at another of the fracture ends and the bone bridge; the second bone nail, the connecting piece, the degradable gasket, the bone bridge, and the fracture ends are configured to be fixedly connected by the bone bridge to form a stable fracture/fixture complex at initial fixation, so as to form a stable static fixation;
   as the degradable gasket is gradually degraded and absorbed in vivo, the connection between the connecting piece and the bone bridge where the degradable gasket is placed gradually loosens therewith; but the positional relationships between the second bone nail as well as the bone bridge and the fracture ends fixed by same are still stable rigid invariable structures; the joint between the connecting piece and the bone bride where the degradable gasket is placed becomes clearance fit; and the fracture ends constrained by the bone bridge, the connecting piece, and the bone nails can also only slide axially along the bone bridge under the action of an external force, that is, the fracture/fixture complex becomes axial non-rigid connection, and the fixation of the whole fixation system also gradually changes to axial non-rigid dynamic fixation.

2. The bone fixation system according to claim 1, wherein the bone bridge is a plate-shaped bone plate, and the bone plate comprises bone nail through holes and a chute;

the connecting piece is a sliding block embedded into the chute of the bone plate, and at least one of the bone nail through holes is formed in the sliding block;

a side wall of the sliding block is a smooth plane; the side wall of the sliding block is matched with an inner wall of the chute in a surface contact manner in a radial direction; there is a sliding clearance between the sliding block and the chute in the axial direction of the bone plate; the degradable gasket is an embedded degradable gasket filling the sliding clearance; and the bone nails are connected with the bone plate through the bone nail through holes in the bone plate and the bone nail through holes in an upper surface of the sliding block attached to the bone plate with smooth common nail heads and threaded locking nail heads, so as to complete the assembly and fixation of the fracture/fixture system.

3. The bone fixation system according to claim 2, wherein the chute is a groove that does not penetrate through the plate surface of the bone plate, and the sliding block is embedded into the groove;

through holes are formed in the bottom of the groove; the through holes are greater than the bone nails in diameter; and when the degradable gasket is gradually degraded, the integrated sliding block and the fracture ends may perform axial movement along the through holes along with the bone holes.

4. The bone fixation system according to claim 3, wherein a laying-type degradable gasket which has the same shape as the bottom surface of the sliding block and is degradable is also arranged between the bottom of the sliding block and the groove; and after the bone nails penetrate through the bone nail through holes in the sliding block and the laying-type degradable gasket is fastened in the bone, the connection between the sliding block and the bone plate is rigid connection.

5. The bone fixation system according to claim 2, wherein the sliding clearance between the sliding block and the chute in the axial direction of the bone plate is 0.2 to 1 mm; the thickness of the embedded degradable gasket is 0.2 to 1 mm; the thickness of the laying-type degradable gasket is 0.1 to 0.5 mm; and the thickness of the tile-type degradable gasket is 0.2 to 1 mm.18.

6. The bone fixation system according to claim 1, wherein the degradable gasket is made of magnesium or zinc or a composite consisting of magnesium and zinc, or a composite consisting of magnesium and polylactic acid coating externally thereon, or a composite consisting of zinc and polylactic acid coating externally thereon, or a composite consisting of the composite consisting of magnesium and zinc and polylactic acid coating externally thereon that may be degraded in vivo; and the degradable gasket is a complete gasket, or a plurality of layers of gaskets made of the same composite material or a plurality of layers of gaskets made of different composite materials are overlaid to use to control the degradation rate.

7. The bone fixation system according to claim 4, wherein the sliding clearance between the sliding block and the chute in the axial direction of the bone plate is 0.2 to 1 mm; the thickness of the embedded degradable gasket is 0.2 to 1 mm; the thickness of the laying-type degradable gasket is 0.1 to 0.5 mm; and the thickness of the tile-type degradable gasket is 0.2 to 1 mm.

* * * * *